(12) United States Patent
Ritter et al.

(10) Patent No.: US 12,396,929 B2
(45) Date of Patent: Aug. 26, 2025

(54) DENTAL COMPOSITION

(71) Applicant: DENTSPLY SIRONA Inc., York, PA (US)

(72) Inventors: Helmut Ritter, Wuppertal (DE); Joachim E. Klee, Radolfzell (DE); Hui Lu, Magnolia, DE (US); Kira Neuhaus, Dusseldorf (DE)

(73) Assignee: Dentsply Sirona Inc., York, PA (US)

( * ) Notice: Subject to any disclaimer, the term of this patent is extended or adjusted under 35 U.S.C. 154(b) by 949 days.

(21) Appl. No.: 17/601,786

(22) PCT Filed: Apr. 9, 2020

(86) PCT No.: PCT/US2020/027417
§ 371 (c)(1),
(2) Date: Oct. 6, 2021

(87) PCT Pub. No.: WO2020/214475
PCT Pub. Date: Oct. 22, 2020

(65) Prior Publication Data
US 2022/0202658 A1    Jun. 30, 2022

Related U.S. Application Data

(60) Provisional application No. 62/833,960, filed on Apr. 15, 2019.

(51) Int. Cl.
*A61K 6/887* (2020.01)
*A61K 6/61* (2020.01)
(Continued)

(52) U.S. Cl.
CPC ............... *A61K 6/887* (2020.01); *A61K 6/61* (2020.01); *A61K 6/62* (2020.01); *A61K 6/71* (2020.01);
(Continued)

(58) Field of Classification Search
CPC .. A61K 6/61; A61K 6/62; A61K 6/887; C08L 33/08; C08L 33/10; C08L 45/00; C08F 32/00–08
See application file for complete search history.

(56) References Cited

U.S. PATENT DOCUMENTS 5,154,762 A    10/1992 Mitra
5,501,727 A    3/1996 Wang
(Continued)

FOREIGN PATENT DOCUMENTS

CA    2297442 A1    8/2000
EP    1815838 A1    8/2007
(Continued)

OTHER PUBLICATIONS

International Search Report; PCT/US2020/027417; Oct. 9, 2020 (completed); Oct. 19, 2020 (mailed).
(Continued)

*Primary Examiner* — Kregg T Brooks
*Assistant Examiner* — David R. Foss
(74) *Attorney, Agent, or Firm* — SCHWEGMAN LUNDBERG & WOESSNER, P.A.

(57) ABSTRACT

Disclosed herein is a dental material containing a polymerizable hydrolysis stable polycyclic amide monomer. The present disclosure relates to methods of making and use of the polymerizable hydrolysis stable polycyclic amide monomer for the preparation of a dental polymerizable hydrolysis stable polycyclic amide monomer composition. The present disclosure further relates to a cured dental material obtained by polymerizing the dental material.

13 Claims, 2 Drawing Sheets

(51) Int. Cl.
  *A61K 6/62* (2020.01)
  *A61K 6/71* (2020.01)
  *C08F 32/00* (2006.01)
  *C08F 32/04* (2006.01)
  *C08F 32/06* (2006.01)
  *C08F 32/08* (2006.01)
  *C08L 33/10* (2006.01)
  *C08L 45/00* (2006.01)
  *C08F 32/02* (2006.01)

(52) U.S. Cl.
  CPC .............. *C08F 32/00* (2013.01); *C08F 32/02* (2013.01); *C08F 32/04* (2013.01); *C08F 32/06* (2013.01); *C08F 32/08* (2013.01); *C08L 33/10* (2013.01); *C08L 45/00* (2013.01)

(56) References Cited

U.S. PATENT DOCUMENTS

| | | | |
|---|---|---|---|
| 5,889,132 | A | 3/1999 | Rheinberger |
| 6,136,887 | A | 10/2000 | Moszner |
| 7,365,222 | B2 | 4/2008 | Moszner |
| 9,580,524 | B2 | 2/2017 | Kitadume |
| 2006/0178469 | A1 | 8/2006 | Moszner |
| 2008/0058443 | A1 | 3/2008 | Moszner |
| 2018/0036209 | A1 | 2/2018 | Moszner |

FOREIGN PATENT DOCUMENTS

| | | |
|---|---|---|
| JP | H1045521 | 2/1998 |
| JP | 2022049375 | 3/2022 |
| JP | 2022529244 | 6/2022 |
| JP | 7556879 | 10/2024 |
| WO | 2020214475 | 10/2020 |

OTHER PUBLICATIONS

Written Opinion of the International Searching Authority; PCT/US2020/027417; Oct. 9, 2020 (completed); Oct. 19, 2020 (mailed).

International Preliminary Report on Patentability; PCT/US2020/027417; Oct. 9, 2020 (completed); Oct. 19, 2020 (mailed).

"Forgotten Monomers: free radical polymerization behavior of norbornadiene derivatives in comparison with methyl methacrylate"; Alupei, V. et al; Polymer, Elsevier Science Publishers B.V., GB; vol. 45, No. 7; Mar. 1, 2004; pp. 2111-2117.

"Probing the origins and control of shrinkage stress in dental resin-composites: I. Shrinkage stress characterization technique"; H. Lu et al; Journal of Materials Science: Materials in Medicine; 2004; vol. 15; pp. 1097-1103.

"Australian Application Serial No. 2020259278, First Examination Report mailed Dec. 17, 2024", 3 pgs.

"Australian Application Serial No. 2020259278, Response filed Feb. 25, 2025 to First Examination Report mailed Dec. 17, 2024", 38 pgs.

"Japanese Application Serial No. 2021-559993, Notification of Reasons for Rejection mailed Apr. 2, 2024", W English Translation, 8 pgs.

"Japanese Application Serial No. 2021-559993, Response filed Jun. 28, 2024 to Notification of Reasons for Rejection mailed Apr. 2, 2024", W English Claims, 14 pgs.

DENTAL COMPOSITION

FIELD OF THE DISCLOSURE

The present disclosure relates to a dental material containing a polymerizable hydrolysis stable polycyclic amide monomer. The present disclosure relates to methods of making and use of the polymerizable hydrolysis stable polycyclic amide monomer for the preparation of a dental polymerizable hydrolysis stable polycyclic amide monomer composition. The present disclosure further relates to a cured dental material obtained by polymerizing the dental material.

BACKGROUND OF THE DISCLOSURE

During dental composite restoration procedures, polymerization shrinkage stress occurred from the composite resin polymerization. The transfer of this polymerization stress to the interface with the tooth leads to many clinical problems such as enamel fractures, compromised bonding, post-operative sensitivity, and secondary caries.

In this context, it is known in the prior art that cyclic monomers like monofunctional vinylcyclopropane derivatives react with significantly lower polymerization stress in comparison with linear monomers, such as (meth)acrylates. During polymerization, monofunctional vinylcyclopropane derivatives polymerize with a ring-opening mechanism. But in general, monofunctional vinylcyclopropane esters have a slow polymerization kinetic.

U.S. Pat. No. 6,136,887 discloses polymerizable vinylcyclopropane derivatives and U.S. Pat. No. 7,365,222 discloses bicyclic cyclopropane derivatives; which display a low volume shrinkage during polymerization and at the same time are radically copolymerizable with (meth)acrylates.

U.S Pat. Appl. No 2018/0036209 discloses radically polymerizable dental materials containing at least one vinylcyclopropane, which shrinks only slightly on radical polymerization and which have a high radical polymerization reactivity, in particular on photopolymerization.

U.S Pat. Appl. No 2008/0058443 discloses dental materials having low polymerization shrinkage and comparable mechanical properties, comprising at least one polymerizable calix[n] arene having polymerizable group, wherein the polymerizable group is a group, which can polymerize under radical conditions, such as (meth)acrylate or (meth)acrylamide, a cyclic group which can polymerize under radical conditions by ring opening, or a group which can polymerize under cationic conditions, such as, e.g., a cycloaliphatic epoxide or oxetane group or a polyreactive nitrone group.

U.S. Pat. No. 9,530,524 discloses a vinylcyclopropane that exhibits volume expansion upon homopolymerization and that enables improved solvent solubility, a monomer composition that contains the vinylcyclopropane, a polymer of the vinylcyclopropane, a polymer composition that contains the polymer, and an article that is obtainable through curing of the monomer composition. The vinylcyclopropane can be suitably used in production of optical materials, molding materials, composite materials, casting materials, sealing materials, medical materials, dental materials, recording materials, cements, coating materials, adhesives, materials for holographic optical recording media, and so forth.

It has been shown by Alupei et al. (Polymer 45 (2004), 2111-2117) that 3-ethoxycarbonyl-tricyclo[3.2.1.0$^{2,4}$] oct-6-ene can be converted in the presence of radical initiators, into a stable polymer with nortricyclene repeating backbone units. Instead of normal vinyl polymerization, the polymerization mechanism is based on intramolecular cyclopropanantion accompanied by a ring opening process and reduce polymerization stress.

By using monofunctional vinylcyclopropane amides, the polymerization rate increases.

Bis (polycyclic amide) compounds adapt this monofunctional vinylcyclopropane structure. The amide structure is hydrolysis stable and have a sufficient polymerization kinetic.

SUMMARY OF THE DISCLOSURE

There is a continued need for development of bulk-fill restorations with simultaneous well-preserved bonding, easy handling and desired esthetic, such as by incorporating a polymerizable hydrolysis stable polycyclic amide monomer as additive in dental compositions.

It is the object of the present disclosure to provide a polymerizable hydrolysis stable polycyclic amide monomer and its use as additive in dental compositions to significantly reduce polymerization stress compared to (meth)acrylates with a comparable double bond content. The compositions containing polymerizable hydrolysis stable polycyclic amide monomer are particularly suitable as dental materials, in particular, as a dental composite material, a dental glass ionomer, a dental sealant, a dental adhesive, an adhesion promoter, an adhesion preventing material, a cement, a crown-forming material, or an impression material.

In a first aspect of the present disclosure, a dental material is provided comprising:
(i) a polymerizable hydrolysis stable polycyclic amide monomer comprising compound of Formula (I)

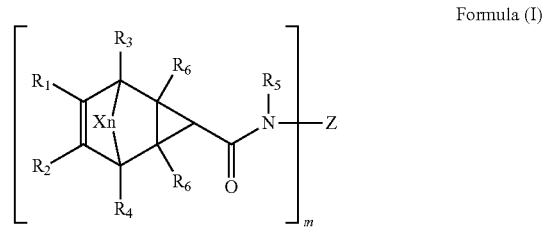

Formula (I)

wherein
$R_1$, $R_2$, $R_3$ and $R_4$ are independent from each other, and represent a hydrogen, a $C_{1-4}$ alkyl group or a $C_5$-$C_{18}$ aryl group;
$R_5$ is a hydrogen atom, a $C_{1-6}$ alkyl group, a $C_{3-10}$ cycloalkyl group, a $C_7$-$C_{12}$ aralkyl group; wherein each group of $R_5$ is optionally substituted by one or more of a $C_{1-4}$ alkyl group, a $C_{1-4}$ alkoxy group, or a hydroxyl group;
$R_6$ is a hydrogen atom, a $C_{1-6}$ alkyl group, a $C_{3-10}$ cycloalkyl group, a $C_7$-$C_{12}$ aralkyl group, a $C_6$-$C_{10}$ aryl group, an ester or an amide group,
X is an alkylene group, O, S, or CO;
n is an integer of from 0 to 1;
m is an integer of from 1 to 6; and
Z is a (m+1)-valent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or an unsubstituted or substituted $C_3$-$C_{18}$ heteroarylene group; wherein each unsubstituted or substituted group of Z optionally includes at least one of 1-6 oxygen, silicon, sulfur atoms, or $NR_9$ wherein $R_9$ represents a hydrogen atom, straight or branched or cyclic $C_{1-6}$ alkyl groups;
(ii) at least one polymerizable resin monomer having at least one (meth)acrylate group, (meth)acrylamide group, allyl group, or vinyl group;
(iii) optionally a particulate filler; and
(iv) at least one of a photoinitiator and a redox initiator.

The present disclosure provides a use of the polymerizable hydrolysis stable polycyclic amide monomer for the preparation of a dental material.

In a second aspect of the disclosure, a method for preparing the polymerizable hydrolysis stable polycyclic amide monomer comprising compound of Formula (I) is provided. The method includes reacting a mixture comprising:
(i) x equivalent of at least one component A having compound of Formula (II)

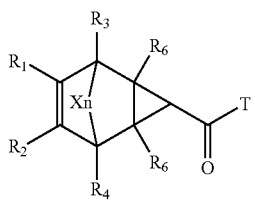

Formula II wherein
$R_1$, $R_2$, $R_3$ and $R_4$ are independent from each other, and represent a hydrogen, a $C_{1-4}$ alkyl group or a $C_5$-$C_{18}$ aryl group;
$R_6$ is a hydrogen atom, a $C_{1-6}$ alkyl group, a $C_{3-10}$ cycloalkyl group, a $C_7$-$C_{12}$ aralkyl group, a $C_6$-$C_{10}$ aryl group, an ester or an amide group,
X is an alkylene group, O, S, or CO;
n is an integer of from 0 to 1; and
T is a hydroxyl group or halogen atom.
(ii) y equivalent of a component B having at least one of primary amine functional group and secondary amine functional group of compounds of Formula III:

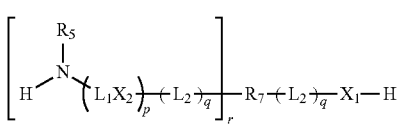

Formula III wherein
$R_7$ is a (r+1)-valent aliphatic $C_{2-10}$ group, cycloaliphatic $C_3$-$C_6$ group or an aralkylene group having 7 to 24 carbon atoms, wherein each group of $R_7$ optionally contains oxygen or sulfur atoms and each group of $R_7$ is optionally substituted by $C_{1-4}$ alkyl groups;
$R_5$ is a hydrogen atom, a $C_{1-6}$ alkyl group, a $C_{3-10}$ cycloalkyl group, a $C_7$-$C_{12}$ aralkyl group, or an (meth) acryl group; wherein each group of $R_5$ is optionally substituted by one or more of a $C_{1-4}$ alkyl group, a $C_{1-4}$ alkoxy group, or a hydroxyl group;
$L_1$ and $L_2$ are independently a same or different straight or branched chain alkylene having from 1 to 4 carbons;
$X_1$ is a direct bond, or a nitrogen atom substituted by $R_5$;
$X_2$ is an oxygen atom;
p and q are an integer of from 0 to 4; and
r is an integer of from 1 to 6;

wherein x and y are molar equivalents of a component (i) and (ii).

to form the polymerizable hydrolysis stable polycyclic amide monomer comprising compound of following Formula (I)

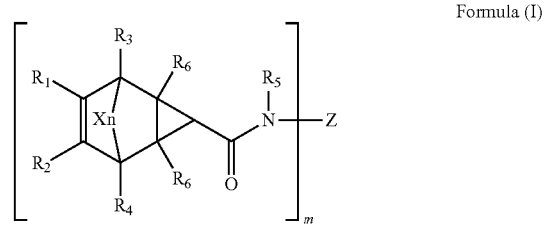

Formula (I)

wherein
$R_1$, $R_2$, $R_3$ and $R_4$ are independent from each other, and represent a hydrogen, a $C_{1-4}$ alkyl group or a $C_5$-$C_{18}$ aryl group;
$R_5$ is a hydrogen atom, a $C_{1-6}$ alkyl group, a $C_{3-10}$ cycloalkyl group, a $C_7$-$C_{12}$ aralkyl group; wherein each group of $R_5$ is optionally substituted by one or more of a $C_{1-4}$ alkyl group, a $C_{1-4}$ alkoxy group, or a hydroxyl group;
$R_6$ is a hydrogen atom, a $C_{1-6}$ alkyl group, a $C_{3-10}$ cycloalkyl group, a $C_7$-$C_{12}$ aralkyl group, a $C_6$-$C_{10}$ aryl group, an ester or an amide group,
X is an alkylene group, O, S, or CO;
n is an integer of from 0 to 1;
m is an integer of from 1 to 6; and
Z is a (m+1)-valent unsubstituted or substituted $C_1$-$C_{18}$ is alkylene group, an unsubstituted or substituted $C_3$-$C_8$ cycloalkylene group, an unsubstituted or substituted aralkylene group, an unsubstituted or substituted $C_5$-$C_{18}$ arylene group or an unsubstituted or substituted $C_3$-$C_{18}$ heteroarylene group; wherein each unsubstituted or substituted group of Z optionally includes at least one of 1-6 oxygen, silicon, sulfur atoms, or $NR_9$, wherein $R_9$ represents a hydrogen atom, straight or branched or cyclic $C_{1-6}$ alkyl groups.

Figure 1:
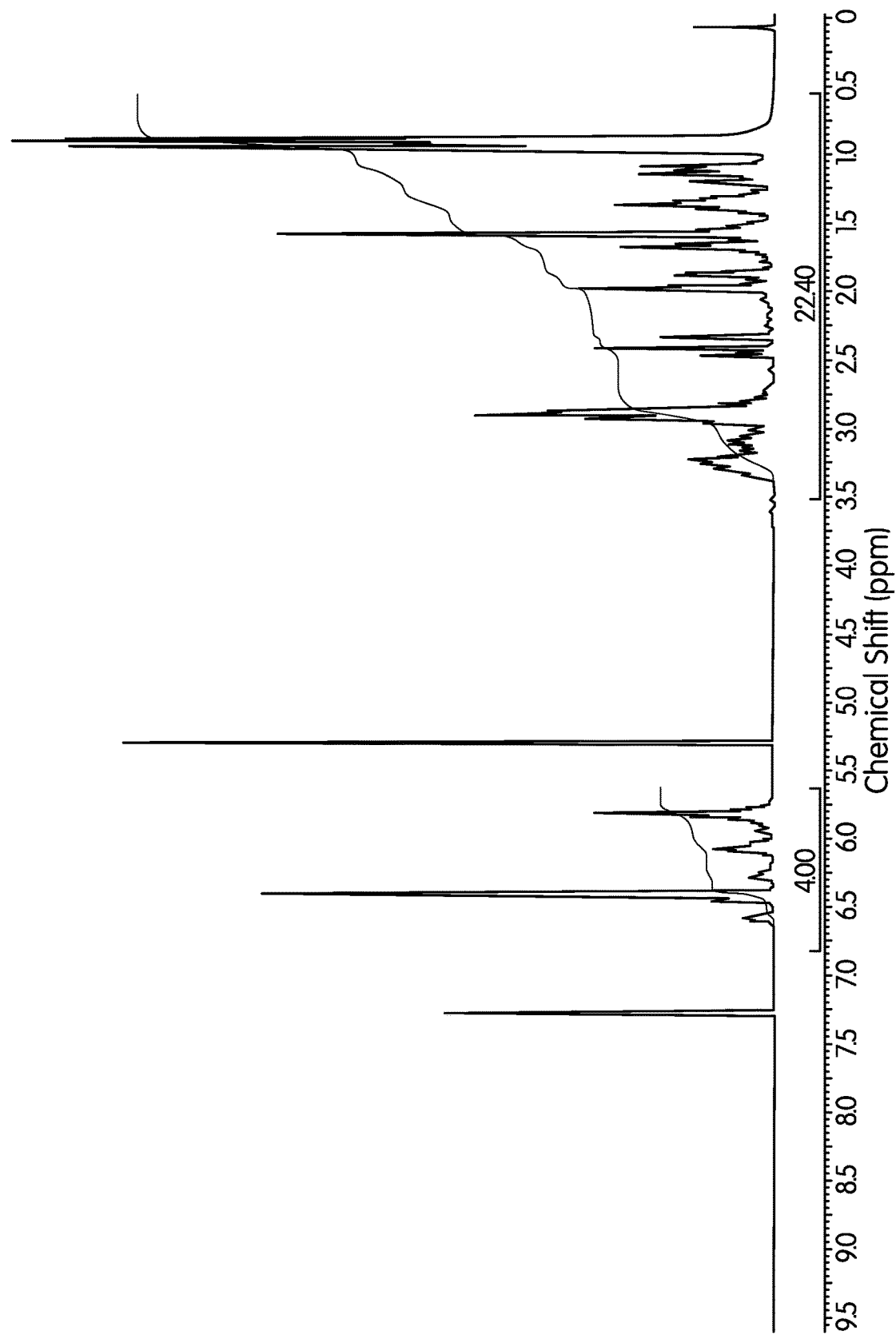
FIG. 1 depicts $^1$H NMR spectrum of bis(Norbornene cyclopropane amido) compound 1 in $CDCl_3$.

Curve 1: t00182 Nov. 6, 2018 2 11 pm tensometer HLU18-150-N5T5_L103118_QHL-2min_S1.tsd
0=number of lines in beam documentation, Curve 2: t00183 Nov. 6, 2018 4 25 pm tensometer HLU18-150-N5T5_L103118_QHL-2min_S2.tsd
0=number of lines in beam documentation, Curve 3: t00008 Oct. 1, 2018 10 24 am tensometer CMX-Resin_K900833_L1802000718_PostRepair_S1.tsd, Curve 4: t00009 Oct. 1, 2018 11 31 am tensometer CMX-Resin_K900833_L1802000718_PostRepair_S2.tsd, Curve 5: t00011 Oct. 1, 2018 2 50 pm tensometer CMX-Resin _K900833_L1802000718_PostRepair_S3.tsd.

DETAILED DESCRIPTION OF THE DISCLOSURE

The above-mentioned aspects, as well as other aspects, features, and advantages of the present disclosure are described below in connection with various embodiments, with reference made to the accompanying figures. Some of the terms used in the present disclosure are defined below:

The term "alkyl", unless otherwise specified, refers to a monoradical branched or unbranched saturated hydrocarbon chain having from 1 to 18 carbon atoms. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, dodecyl, tetradecyl, and the like. Alkyl groups may be substituted further with one or more substituents selected from alkenyl, alkoxy, and hydroxyl.

The term "alkylene", unless otherwise specified refers to a linear saturated divalent hydrocarbon radical of one to eighteen carbon atoms or a branched saturated divalent hydrocarbon radical of three to eighteen carbon atoms, e.g., methylene, ethylene, 2,2-dimethylethylene, propylene, 2-methylpropylene, butylene and the like, preferably methylene, ethylene, or propylene.

The term "alkoxy" is a functional group containing an alkyl group bonded to an oxygen atom. The $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

The term "arylene" is the divalent moiety of 'aryl'. The term "aryl" refers to $C_5$-$C_{18}$-membered aromatic, heterocyclic, fused aromatic, fused heterocyclic, biaromatic, or biheterocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those "aryl" groups having heteroatoms in the ring structure may also be referred to as "heteroaryl" or "heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamide, ketone, aldehyde, ester, heterocyclyl, aromatic or heteroaromatic moieties, —$CF_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

The term "heteroarylene" is the divalent moiety of "heteroaryl".

The term "aralkylene" is the divalent moiety of "aralkyl". The term "aralkyl" refers to a radical of the formula —R'-aryl, where R' is an alkylene as defined above, for example methylene, ethylene and the like. The aryl part is optionally substituted as described above for aryl group.

The term "cycloalkylene" is the divalent moiety of "cycloalkyl". The term "cycloalkyl" refers to monocyclic or polycyclic cycloalkyl radical. Examples of monocyclic cycloakyl include cyclopropyl, cyclobutyl, cyclopentyl, cyclohexyl, cycloheptyl, and cyclooctyl. Examples of polycyclic cycloalkyl radical include, for example admantyl, norbornyl, decalinyl, 7,7-dimethyl-bicyclo[2.2.1]heptanyl, tricyclo[5.2.1.0$^{2,6}$]decyl and the like. Unless otherwise stated specifically in the specification, the term "cycloalkyl" is meant to include monocyclic or polycyclic cycloalkyl radical that are optionally substituted by one or more substituents selected from alkyl, halo, oxo or alkylene chain.

The term "cycloalkylalkylene" refers to group —R'-cycloalkyl-" where R' is an alkylene as defined above, for example methylene, ethylene and the like. As used herein $C_1$-$C_8$ cycloalkylalkylene refers to a cycloalkyl linked through a $C_1$-$C_8$ alkylene group.

The term "divalent hydrocarbon radical" refers to divalent hydrocarbon radicals having 2 to 18 carbon atoms include alkylene radicals such as ethylene, methylmethylene, propylene, butylene, pentylene, hexylene and octadecylene; alkylene radicals such as vinylene, allylene and butadienylene; cycloalkylene radicals such as cyclobutylene, cyclopentylene and cyclohexylene; cycloalkenylene radicals such as cyclopentenylene and cyclohexenylene; arylene radicals such as phenylene and xenylene; aralkylene radicals as benzylene; and alkarylene radicals such as tolylene.

The term "polymerizable moiety", regarding free radical polymerization, frequently refers to any double bond capable of addition polymerization, such as carbon-carbon double bond.

The term "(meth)acrylate" in the context of the present disclosure is meant to refer to the acrylate as well as to the corresponding methacrylate.

The term "(meth)acryl" in the context of the present disclosure is meant to refer to the acryl as well as to the corresponding methacryl.

The present disclosure relates to a dental material containing a polymerizable hydrolysis stable polycyclic amide monomer. The present disclosure relates to methods of making the polymerizable hydrolysis stable polycyclic amide monomer. The present disclosure relates to use of the polymerizable hydrolysis stable polycyclic amide monomer for the preparation of a dental polymerizable hydrolysis stable polycyclic amide monomer composition. The compositions containing polymerizable hydrolysis stable polycyclic amide monomer are particularly suitable as dental materials, in particular, as a dental composite material, a dental glass ionomer, a dental sealant, a dental adhesive, an adhesion promoter, an adhesion preventing material, a cement, a crown-forming material, or an impression material.

In an aspect of the present disclosure there is provided a dental material comprising:

(i) a polymerizable hydrolysis stable polycyclic amide monomer comprising compound of Formula (I)

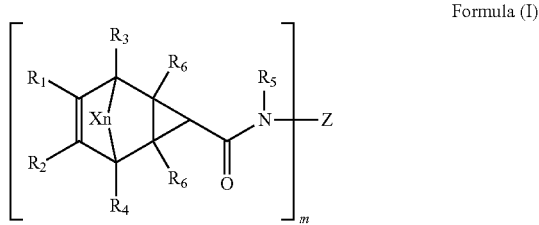

Formula (I)

wherein $R_1$, $R_2$, $R_3$ and $R_4$ are independent from each other, and represent a hydrogen, a $C_{1-4}$ alkyl group or a $C_5$-$C_{18}$ aryl group;

$R_5$ is a hydrogen atom, a $C_{1-6}$ alkyl group, a $C_{3-10}$ cycloalkyl group, a $C_7$-$C_{12}$ aralkyl group; wherein each group of $R_5$ is optionally substituted by one or more of a $C_{1-4}$ alkyl group, a $C_{1-4}$ alkoxy group, or a hydroxyl group;

$R_6$ is a hydrogen atom, a $C_{1-6}$ alkyl group, a $C_{3-10}$ cycloalkyl group, a $C_7$-$C_{12}$ aralkyl group, a $C_6$-$C_{10}$ aryl group, an ester or an amide group, X is an alkylene group, O, S, or CO;

n is an integer of from 0 to 1;

m is an integer of from 1 to 6; and

Z is a (m+1)-valent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or an unsubstituted or substituted $C_3$-$C_{18}$ heteroarylene group; wherein each unsubstituted or substituted group of Z optionally includes at least one of 1-6 oxygen, silicon, sulfur atoms, or $NR_9$, wherein $R_9$ represents a hydrogen atom, straight or branched or cyclic $C_{1-6}$ alkyl groups;

(ii) at least one polymerizable resin monomer having at least one (meth)acrylate group, (meth)acrylamide group, allyl group, or vinyl group;

(iii) optionally a particulate filler; and (iv) at least one of a photoinitiator and a redox initiator.

1. A Polymerizable Hydrolysis Stable Polycyclic Amide Monomer

A polymerizable hydrolysis stable polycyclic amide monomer is a compound of Formula (I)

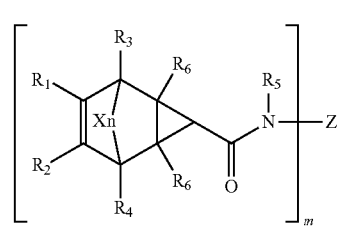

Formula (I)

wherein $R_1$, $R_2$, $R_3$ and $R_4$ are independent, from each other, and represent a hydrogen, a $C_{1-4}$ alkyl group or a $C_5$-$C_{18}$ aryl group;

$R_5$ is a hydrogen atom, a $C_{1-6}$ alkyl group, a $C_{3-10}$ cycloalkyl group, a $C_7$-$C_{12}$ aralkyl group; wherein each group of $R_5$ is optionally substituted by one or more of a $C_{1-4}$ alkyl group, a $C_{1-4}$ alkoxy group, or a hydroxyl group;

$R_6$ is a hydrogen atom, a $C_{1-6}$ alkyl group, a $C_{3-10}$ cycloalkyl group, a $C_7$-$C_{12}$ aralkyl group, a $C_6$-$C_{10}$ aryl group, an ester or an amide group, X is an alkylene group, O, S, or CO;

n is an integer of from 0 to 1;

m is an integer of from 1 to 6; and

Z is a (m+1)-valent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or an unsubstituted or substituted $C_3$-$C_{18}$ heteroarylene group; wherein each unsubstituted or substituted group of Z optionally includes at least one of 1-6 oxygen, silicon, sulfur atoms, or $NR_9$, wherein $R_9$ represents a hydrogen atom, straight or branched or cyclic $C_{1-6}$ alkyl groups.

The term "polymerizable hydrolysis stable polycyclic amide monomer" is meant to contain more than one cyclic moiety containing cyclopropyl group and an amide group. The polycyclic amide monomers are hydrolysis stable. Specifically, the polymerizable polycyclic amide monomers do not contain groups such as esters, in the main chain which hydrolyze in aqueous media under acidic condition, at a temperature of about 23 to 27° C. within one month. Acidic condition refers to a pH of 1 to 5, such as 2 to 4, or at pH 3.

In certain embodiments, the polymerizable polycyclic amide monomer is a polycyclo olefin containing cyclopropyl group having a compound of Formula I, wherein $R_1$, $R_2$, $R_3$, $R_4$ and $R_6$ is a hydrogen; X is alkylene and n is 1.

In one particular embodiment, the polymerizable polycyclic amide monomer is a norbornene-type moiety containing cyclopropyl group having compound of Formula I, wherein $R_1$, $R_2$, $R_3$, $R_4$ and $R_6$ is a hydrogen; X is methylene and n is 1.

In one embodiment, the polymerizable polycyclic amide is a substituted tricyclo[3.2.1.0$^{2,4}$] oct-6-ene containing monomer.

In one particular embodiment, the polymerizable polycyclic amide monomer is a compound of formula I, wherein m is 1 and $R_5$ is a hydrogen.

In certain embodiment of compound of Formula I, Z is unsubstituted or substituted $C_1$-$C_{18}$ alkylene group, which may optionally include at least one of 1-6 oxygen, silicon, sulfur atoms, or $NR_9$, wherein $R_9$ represents a hydrogen atom, straight or branched or cyclic $C_{1-6}$ alkyl groups.

In one embodiment, Z represents a group according to a Formula IV

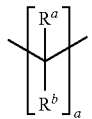

Formula IV wherein
$R^a$ and $R^b$ are independently same or different hydrogen atom, a $C_{1-6}$ linear or branched alkyl group, or a $C_{4-10}$ aryl group; and
a is an integer of from 1 to 18.

In one particular embodiment, Z is selected from

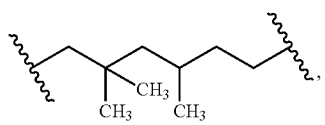

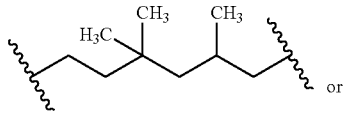 or

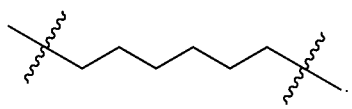

In certain embodiments, Z represents a group according to a Formula V

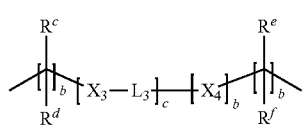

Formula V wherein
$R^c$, $R^d$, $R^e$ and $R^f$ are independently same or different hydrogen atom, a $C_{1-6}$ linear or branched alkyl group, or a $C_{4-10}$ aryl group;
$X_3$ and $X_4$ are independently same or different an oxygen atom, a sulfur atom and a group $NR_9$, wherein $R_9$ is a hydrogen atom or a $C_{1-4}$ alkyl group;
$L_3$ is a divalent hydrocarbon radical selected from linear or branched $C_{2-3}$ alkylene group or $C_5$-$C_{18}$ arylene group.
b is an integer of from 1 to 10;
c is an integer of from 1 to 10; and
d is an integer of from 0 to 1.

In certain embodiment, Z represents a group according to a Formula VI

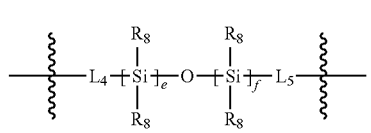

Formula VI wherein
$R_8$ represent a straight chain, branched or cyclic alkyl group.
$L_4$ and $L_5$ are independently same or different $C_{2-20}$ alkylene group;
e is an integer of from 1 to 10; and
f is an integer of from 0 to 1.

Compound of Formula I may be selected from the following compounds:

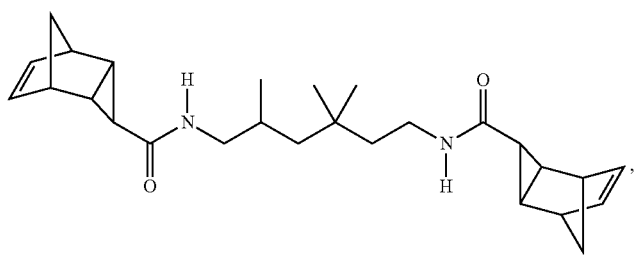

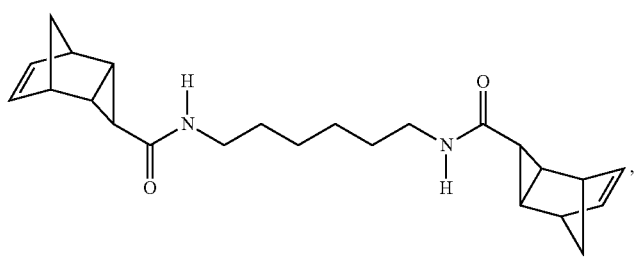

-continued

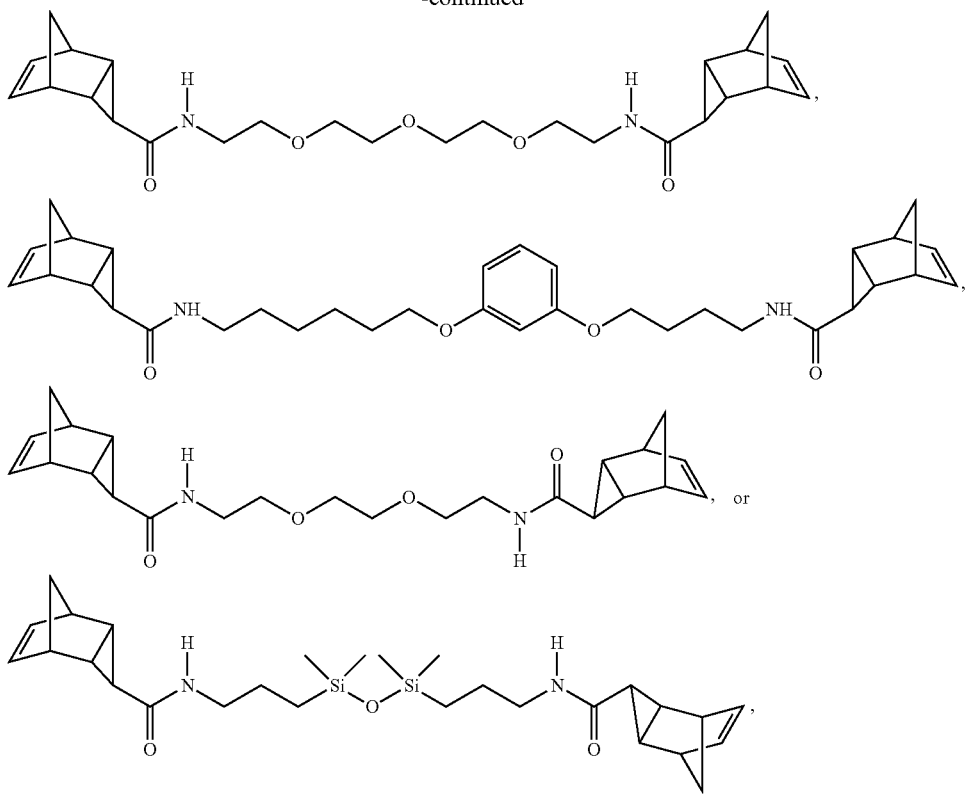

In one embodiment of the dental material disclosed herein, the polymerizable hydrolysis stable polycyclic amide monomer may be present in an amount of from 1 to 99% based on total weight of the dental material. Alternatively, in the range of from 2 to 95%; alternatively, in the range of from 5 to 90% or any value, range, or sub-range there between, based on the total weight of the dental material.

In an aspect of the present disclosure, a method of preparing the polymerizable hydrolysis stable polycyclic amide monomer having a compound of Formula I are described.

In one embodiment, the compound of formula (I) is obtained by reacting a mixture comprising:
(i) x equivalent of at least one component A having compound of Formula (II)

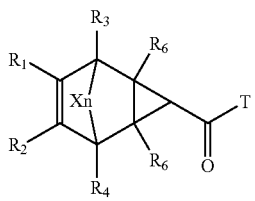

Formula II wherein
$R_1$, $R_2$, $R_3$ and $R_4$ are independent from each other, and represent a hydrogen, a $C_{1-4}$ alkyl group or a $C_5$-$C_{18}$ aryl group;
$R_6$ is a hydrogen atom, a $C_{1-6}$ alkyl group, a $C_{3-10}$ cycloalkyl group, a $C_7$-$C_{12}$ aralkyl group, a $C_6$-$C_{10}$ aryl group, an ester or an amide group,
X is an alkylene group, O, S, or CO;
n is an integer of from 0 to 1; and
T is a hydroxyl group or halogen atom.
(ii) y equivalent of a component B having at least one of primary amine functional group and secondary amine functional group of compounds of Formula III:

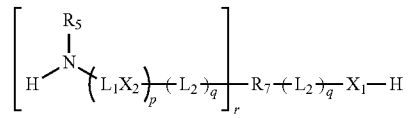

Formula III wherein
$R_7$ is a (r+1)-valent aliphatic $C_{2-10}$ group, cycloaliphatic $C_3$-$C_6$ group or an aralkylene group having 7 to 24 carbon atoms, wherein each group of $R_7$ optionally contains oxygen or sulfur atoms and each group of $R_7$ is optionally substituted by $C_{1-4}$ alkyl groups;
$R_5$ is a hydrogen atom, a $C_{1-6}$ alkyl group, a $C_{3-10}$ cycloalkyl group, a $C_7$-$C_{12}$ aralkyl group, or an (meth) acryl group; wherein each group of $R_5$ is optionally substituted by one or more of a $C_{1-4}$ alkyl group, a $C_{1-4}$alkoxy group, or a hydroxyl group;
$L_1$ and $L_2$ are independently a same or different straight or branched chain alkylene having from 1 to 4 carbons;
$X_1$ is a direct bond, or a nitrogen atom substituted by $R_5$;
$X_2$ is an oxygen atom;
p and q are integer of from 0 to 4; and
r is an integer of from 1 to 6.
wherein x and y are molar equivalents of component (i) and (ii).

In one embodiment, the component A having compound of Formula (II) may be Norbornene cyclopropane carboxylic acid or Norbornene cyclopropane carbonyl halide.

The halide may be selected from bromine or chlorine.

In a specific embodiment, the component. A having compound of Formula (II) may be Norbornene cyclopropane carbonyl chloride.

In one embodiment of the dental material disclosed herein, the component B having at least one of primary amine functional group and secondary amine functional group is a compound of Formula II:

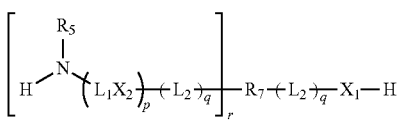

Formula III wherein
- $R_7$ is a (r+1)-valent aliphatic $C_{2-10}$ group, cycloaliphatic $C_3$-$C_6$ group or an aralkylene group having 7 to 24 carbon atoms, wherein each group of $R_7$ optionally contains oxygen or sulfur atoms and each group of $R_7$ is optionally substituted by $C_{1-4}$ alkyl groups;
- $R_5$ is a hydrogen atom, a $C_{1-6}$alkyl group, a $C_{3-10}$ cycloalkyl group, a $C_7$-$C_{12}$ aralkyl group, or an (meth) acryl group; wherein each group of $R_5$ is optionally substituted by one or more of a $C_{1-4}$ alkyl group, a $C_{1-4}$alkoxy group, or a hydroxyl group;
- $L_1$ and $L_2$ are independently a same or different straight or branched chain alkylene having from 1 to 4 carbons;
- $X_1$ is a direct bond, or a nitrogen atom substituted by $R_5$;
- $X_2$ is an oxygen atom;
- p and q are integer of from 0 to 4; and
- r is an integer of from 1 to 6.

The phrase "at least one of primary amine functional group and secondary amine functional group" should be understood to mean "only primary amine functional group", "only secondary amine functional group", or "both primary amine functional group and secondary amine functional group".

In one embodiment of Formula III, $R_7$ is a (r+1)-valent aliphatic $C_{2-10}$ group, cycloaliphatic $C_3$-$C_6$ group or an aralkylene group having 7 to 24 carbon atoms. $R_7$ may be divalent (r=1), trivalent (r=2), tetravalent (r=3), pentavalent (r=5), hexavalent (r=5) or heptavalent (r=6).

In certain embodiment of the dental material disclosed herein, the compound of Formula III may be a diamine of Formula IIIa:

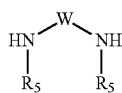

Formula IIIa wherein $R_5$ is as defined above; and
W is divalent aliphatic $C_{2-10}$ group, cycloaliphatic $C_3$-$C_6$ group or an aralkylene group having 7 to 24 carbon atoms, wherein each group optionally contains oxygen or sulfur atoms, and which is optionally substituted by $C_{1-4}$ alkyl groups.

In certain embodiment of the dental material disclosed herein, the compound of Formula III may be a compound of Formula IIIb:

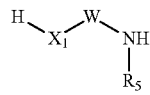

Formula IIIb wherein $R_5$ and $X_1$ are as defined above.

In certain embodiment of the dental material disclosed herein, the compound of Formula III may be a monoamine of Formula IIIc:

Formula IIIc wherein $R_5$ is a monovalent aliphatic $C_{1-10}$ group, cycloaliphatic $C_3$-$C_6$ group or an aralkylene group having 7 to 24 carbon atoms.

In certain embodiment of the dental material disclosed herein, the compound of Formula III may be an amine of Formula IIId:

Formula IIId wherein $R_5$ and $R_7$ are as defined above.

Compound of Formula III may be selected from ethylene diamine, propylene diamine, butylene diamine, pentamethylene diamine, hexamethylene diamine, heptamethylene diamine, tetramethylene diamine, octamethylene diamine, trimethylhexamethylene diamine, diethylene triamine, triethylene tetraamine, tetraethylene pentamine 4,7,10-trioxa-1,13-tridecane diamine, 2,2'-(ethylendioxy) diethylamine, 1,3-bis-(aminomethyl) cyclohexane, 1,3-bis-(4-aminophenoxy)benzene, 4,4'-methylene bis-cyclohexylamine, 5-amino-1,3,3-trimethylcyclohexanemethylamine, Jeffamine T403, Jeffamine T3000, Jeffamine T5000, amino alcohol, propanol amine, N,N'-dimethyl ethylene diamine, N,N'-dibenzyl ethylene diamine, N,N'-dibenzyl 5-oxanonane diamine-1,9, N,N'-dibenzyl 3,5-dioxaoctane diamine-1,8, N,N'-diethyl propane diamine, N,N'-dimethyl propylene diamine, n-butylamine, hexylamine, cyclohexylamine, or benzylamine.

In certain embodiments of the method of preparing the polymerizable hydrolysis stable polycyclic amide monomer having a compound of Formula I, x equivalent of at least one component A having compound of Formula (II) and y equivalent of a component B having at least one of primary amine functional group and secondary amine functional group of compound of Formula III may be dissolved in a solvent and stirred at a reaction temperature.

In certain embodiments of the method of preparing the polymerizable hydrolysis stable polycyclic amide monomer having a compound of Formula I, the solvent may be selected from the group consisting of dichloromethane, tetrahydrofuran, chloroform, dimethyl sulfoxide, and dimethylformamide. The reaction temperature may be, for example from 0° C. to 60° C., such as from 30° C. to 55° C.

In the preparation of the polymerizable hydrolysis stable polycyclic amide monomer having a compound of Formula I a base may be used. The base is selected from the group consisting of triethylamine, 1,4-Diazabicyclo[2.2.2]octane, diisopropylethylamine, and dimethylamino pyridine.

The Filler

The dental material of the present disclosure may include a particulate filler. A "particulate filler" is a powdered metal oxide or hydroxide, mineral silicate, or ion leachable glass or ceramic. Examples of particulate fillers may be selected from fillers currently used in dental restorative compositions.

The particulate filler may have a unimodal or polymodal (e.g., bimodal) particle size distribution. The particulate filler can be an inorganic material. It can also be a cross-linked organic material that is insoluble in the polymerizable resin and is optionally filled with inorganic filler. The particulate filler can be radiopaque, radiolucent or non-radiopaque.

Examples of suitable particulate inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titanic, and zinc glass, and sub-micron silica particles such as pyrogenic silicas.

Examples of suitable filler particles include, but are not limited to, strontium silicate, strontium borosilicate, barium silicate, barium borosilicate, barium fluoroalumino borosilicate glass, barium alumino borosilicate, calcium silicate, calcium alumino sodium fluoro phosphor-silicate lanthanum silicate, alumino silicate, and the combination comprising at least one of the foregoing fillers. The filler particles can further comprise fumed silica. Examples of fumed silica include OX-50 from DeGussa AG (having an average particle size of 40 nm), Aerosil R-972 from DeGussa AG (having an average particle size of 16 nm), Aerosil 9200 from DeGussa AG (having an average particle size of 20 nm), other Aerosil fumed silica might include Aerosil 90, Aerosil 150, Aerosil 200, Aerosil 300, Aerosil 380, Aerosil 8711, Aerosil R7200, and Aerosil R8200, and Cab-O-Sil M5, Cab-O-Sil TS-720, Cab-O-Sil TS-610 from Cabot Corp. Examples of suitable particulate organic filler particles include filled or unfilled pulverized polycarbonates or polyepoxides.

The filler particles used in the material disclosed herein may be surface treated before they are blended with organic compounds. The surface treatment using silane coupling agents or other compounds are beneficial as they enhance the bond between the particulate filler and the matrix and enable the filler particles to be more uniformly dispersed in the organic resin matrix, and also improve physical and mechanical properties. Suitable silane coupling agents include 3-methacryloxypropyltrimethoxysilane, methacryloxyoctyltrimethoxysilane, styrylethyltrimethoxsilane, 3-mercaptopropyltrimethoxysilane, gamma-mercaptopropyltriethoxysilane, gamma-aminopropyltrimethoxysilane and mixtures thereof.

The particulate filler usually has an average particle size of from 0.005 to 100 µm, such as of from 0.01 to 40 µm as measured using, for example, by electron microscopy or by using a conventional laser diffraction particle sizing method as embodied by a MALVERN Mastersizer S or MALVERN Mastersizer 2000 apparatus.

The dental composition of the present disclosure may contain nano-scale particles. As the nano-scale particles in the present disclosure, any known nano-scale particles used in dental compositions may be used without any limitation. Preferable examples of the nano-scale particles include particles of inorganic oxides such as silica, alumina, titania, zirconia, particles of composite oxides of any of these oxides, and particles of calcium phosphate, hydroxyapatite, yttrium fluoride and ytterbium fluoride. Preferably, the nano-scale particles are particles of silica, alumina, titania, prepared by flame pyrolysis.

The average particle size of the nano-scale particles is 1 to 50 nm, such as 3 to 40 nm. The average particle size of the nano-scale particles can be measured by taking electron micrographs of these nano-scale particles and calculating the average value of the diameters of the 100 randomly selected nano-scale particles. It is desirable that the inorganic nano-scale particles be subjected previously to surface treatment with a surface treating agent to improve the affinity between the inorganic filler and the polymerizable composition of the present disclosure, and to increase the chemical bonding between the inorganic filler and the polymerizable composition so as to enhance the mechanical strength of the cured product.

In one embodiment, the particulate filler may be organically modified silica nanoparticles diluted with ethoxylated bis-phenol A dimethacrylate (Ormosil II).

The dental material of the present disclosure may include the particulate filler in an amount of from 10 to 90% w/w based on total weight of the dental material. Alternatively, in the range of from 30 to 85% or any value, range, or sub-range there between, based on the total weight of the dental material.

The Photoinitiators

The dental material of the present disclosure includes at least one of photoinitiator and redox initiator.

The phrase "at least one of photoinitiator and redox initiator" should be understood to mean "only photoinitiator", "only redox initiator", or "both photoinitiator and redox initiator".

Suitable photoinitiators include Type I and Type II. They can be used independently or as mixture of different photoinitiators plus additional co-initiators. Some preferred photosensitizers may include monoketones and diketones (e.g. alpha diketones) that absorb some light within a range of about 300 nm to about 800 nm (such as, about 400 nm to about 500 nm) such as camphorquinone, benzil, furil, 3,3, 6,5-tetramethylcyclohexanedione, phenanthraquinone and other cyclic alpha diketones. Of these camphorquinone is typically preferred. Preferred electron donor compounds include substituted amines, e.g., ethyl 4-(N, N-dimethyl-amino) benzoate as the accelerator.

According to a further preferred embodiment, the photo initiator further comprises an iodonium compound of the following formula-:

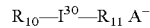

wherein $R_{10}$ and $R_{11}$ which are independent from each other, represent an organic moiety, and $A^-$ is an anion;

For example, diaryl iodonium salt may be selected from (4-methylphenyl)[4-(2-methylpropyl) phenyl] iodonium hexafluoroantimonate, (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di-(4-t-butylphenyl)-iodonium hexafluorophosphate, Bis(4-tert-butylphenyl)iodonium p-toluenesulfonate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl)iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly, iodonium compounds include diphenyliodonium (DPI) hexafluorophosphate, di(4-methylphenyl)iodonium (Me2-DPI) hexafluorophosphate, di-(4-t-butylphenyl)-iodonium hexafluorophosphate diaryliodonium hexafluoroantimonate, (4-methylphenyl)[4-(2-methylpropyl) phenyl] iodonium hexafluoroantimonate, (4-methylphenyl)[4-(2-methylpropyl)phenyl]iodonium hexafluorophosphate (Irgacure 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-isopropyl-4'-methyldiphenyliodonium borate.

According to a particular embodiment, the iodonium compound is di(4-methylphenyl) iodonium (Me2-DPI) hexafluorophosphate.

Other suitable photoinitiators for polymerizing free radically photopolymerizable compositions may include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm may include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl) butanone (IRGACURE 369), 2-methyl-1-[4-(methylthio) phenyl]-2-morpholinopropan-1-one (IRGACURE 907), 2-hydroxy-2-methyl-1-phenyl propan-1-one (DAROCUR 1173), bis(2,4,5-trimethylbenzoyl) phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X).

A suitable redox initiator comprises a reducing and oxidizing agent, which typically reacts with or otherwise cooperate with one another to produce free-radicals capable of initiating polymerization of polymerizable double bonds in a dark reaction, independent from the presence of light. The reducing and oxidizing agents are selected so that the polymerization initiator system is sufficiently storage-stable and free of undesirable colorization to permit storage and use under typical dental conditions. Moreover, the reducing and oxidizing agents are selected so that the polymerization initiator system is sufficiently miscible with the resin system to permit dissolution of the polymerization initiator system in the composition.

Useful reducing agents include ascorbic acid, ascorbic acid derivatives, and metal complexed ascorbic acid compounds as described in U.S. Pat. No. 5,501,727; amines, namely tertiary amines, for example 4-tert-butyl dimethylaniline. Other secondary reducing agents may include cobalt (II) chloride, ferrous chloride, ferrous sulfate, hydrazine, hydroxylamine, salts of a dithionite or sulfite anion, and mixtures thereof.

Suitable oxidizing agents include persulfuric acid and salts thereof, for example, ammonium, sodium, potassium, cesium, and alkyl ammonium salts. Additional oxidizing agents include peroxides, for example, benzoyl peroxides, hydroperoxides, for example, cumyl hydroperoxide, t-butyl hydroperoxide, tert-butylperoxy (2-ethylhexyl)carbonate, tert-butylhydroperoxide, di(tert-butyl)peroxide, tert-butylperoxy-3,5,5-trimethyl-hexanoate, amyl hydroperoxide and potassium peroxydisulfate, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the polymerization initiator system.

Small quantities of transition metal compounds may also be added to accelerate the rate of redox cure. Transition metal compounds may be salt of V, Fe, Cu, Ti, Mn, Ni and Zn. Most preferably, transition metal salt of Fe or Cu. Tetravalent and/or pentavalent vanadium compounds are preferred, including vanadium(IV) oxide, vanadyl(IV) acetylacetonate, vanadyl(IV) oxalate, vanadyl(IV) sulfate, oxobis(1-phenyl-1,3-butanedionato)vanadium(IV), bis(maltolato)oxovanadium(IV), vanadium(V) oxide, sodium metavanadate(V), and ammonium metavanadate(V). Examples of the copper compounds include copper acetylacetonate, copper (II) acetate, copper oleate, copper (II) chloride, and copper (II) bromide.

The redox initiator system may optionally include polymerization accelerators.

Polymerization accelerators is selected from aromatic sulfonic salts, sulfites, hydrogen sulfites, and thiourea compounds.

Examples of aromatic sulfonic salts that may be used as the polymerization accelerator include but are not limited to p-toluenesulfonic salts for example, sodium p-toluenesulfinate, potassium p-toluenesulfinate, calcium p-toluenesulfinate; benzenesulfinic salts, for example, sodium benzenesulfinate, potassium benzenesulfinate, calcium benzenesulfinate, 2,4,6-triethylbenzenesulfinic acid, sodium 2,4,6-triethylbenzenesulfinate, potassium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, and calcium 2,4,6-triisopropylbenzenesulfinate.

Examples of sulfites that may be used as the polymerization accelerator include but are not limited to sodium sulfite, potassium sulfite, calcium sulfite, ammonium sulfite, sodium hydrogen sulfite, and potassium hydrogen sulphite.

Examples of thiourea that may be used as the polymerization accelerator include but are not limited to 1-ethyl-2-thiourea, 1-(2-pyridyl)-2-thiourea, thiourea, ethylthiourea, methylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethyithiourea, tetraethylthiourea, tetra-n-propylthiourea, tetracyclohexylthiourea, 3,3-dimethylethylenethiourea, 4,4-dimethyl-2-imidazolinethione, 1,1-dibutyl thiourea, 1,3-dibutyl thiourea; and mixtures thereof.

The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

A dual cure initiator system combines a photoinitiator system and a redox initiator system.

In one embodiment of the dental material, the at least one of photoinitiator and redox initiator may be present in an amount of from 0.1 weight percent to about 5 weight percent of the dental material.

Homopolymerization/Copolymerization

The polymerizable hydrolysis stable polycyclic amide monomer according to the present disclosure may be polymerized alone or in admixture with radically polymerizable monomers.

Polymerizable Monomer

In one embodiment of the dental material, the polymerizable monomer may be present in an amount of from 1 weight percent to about 99 weight percent of the dental material.

Polymerizable monomers may be acrylates, methacrylates, ethylenically unsaturated compounds, carboxyl group-containing unsaturated monomers, $C_{2-8}$ hydroxyl alkyl esters of (meth)acrylic acid, $C_{1-24}$ alkyl esters or cycloalkyl esters of (meth)acrylic acid, $C_{2-18}$ alkoxyalkyl esters of (meth)acrylic acid, olefins or diene compounds, monoesters/diesters, monoethers, adducts, vinyl monomer, styryl monomer, TPH resin, SDR Resin, PBA resins and/or BPA-free resins.

Examples of specific acrylate monomer include, but are not limited to, methyl acrylate, ethyl acrylate, propyl acrylate, isopropyl acrylate, 2-hydroxyethyl acrylate, hydroxypropyl acrylate, tetrahydrofurfuryl acrylate, glycidyl acrylate, glycerol mono- and di-acrylate, ethyleneglycol diacrylate, polyethyleneglycol diacrylate, neopentyl glycol diacrylate, trimethylolpropane triacrylate, mono-, di-, triacrylate, mono-, di-, tri-, and tetra-acrylates of pentaerythritol and dipentaerythritol, 1,3-butanediol diacrylate, 1,4-butanedioldiacrylate, 1,6-hexane diol diacrylate, 2,2'-bis[3(4-phenoxy)-2-hydroxypropane-1-acrylate]propane, 2,2'-bis(4-acryloxyphenyl)propane, 2,2'-bis[4(2-hydroxy-3-acryloxy-phenyl)]propane, 2,2'-bis(4-acryloxyethoxyphenyl)propane, 2,2'-bis(4-acryloxypropoxyphenyl)propane, 2,2'-bis(4-acryloxydiethoxyphenyl)propane, 2'-bis[3(4-phenoxy)-2-hydroxypropane-1-acrylate]propane, and dipentaerthritol pentaacrylate esters.

Examples of specific conventional methacrylate monomer include, but are not limited to, methyl methacrylates, ethyl methacrylate, propyl methacrylate, isopropyl methacrylate, tetrahydrofurfuryl methacrylate, glycidyl methacrylate, the diglycidyl methacrylate of bis-phenol A (2,2-Bis[4-(2-hydroxy-3-methacryloxypropoxy)phenyl]propane) (Bis-GMA), 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy]ethyl ester (CAS no. 72869-86-4) (UDMA), glycerol mono- and di-methacrylate, ethyleneglycol dimethacrylate, polyethyleneglycol dimethacrylate, triethylene glycol dimethacrylate (TEGDMA), neopentylglycol dimethacrylate, trimethylol propane trimethacrylate, mono-, di-, tri-, and tetra-methacrylates of pentaerythritol and dipentaerythritol, 1,3-butanediol dimethacrylate, 1,4-butanediol dimethacrylate, Bis[2-(methacryloyloxy)ethyl]phosphate (BisMEP), 1,6-hexanediol dimethacrylate, 2-2'-bis(4-methacryloxyphenyl)propane, 2,2'-bis[4 (2-hydroxy-3-methacryloxy-phenyl)]propane, 2,2'-bis(4-methacryloxyethoxyphenyl)propane, 2,2'-bis(4-methacryloxypropoxyphenyl)propane, 2,2'-bis(4-methacryloxydiethoxyphenyl)propane, 2,2'-bis[3(4-phenoxy)-2-hydroxypropane-1-methacrylate]propane, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, and methylene-bis-1-chloromethyl-2-methacryloxyethyl-4-cyclohexyl carbamate.

Examples of ethylenically unsaturated compounds include, but are not limited to, acrylic acid esters, methacrylic acid esters, hydroxy-functional acrylic acid esters, hydroxy-functional methacrylic acid esters, halogen, and hydroxy containing methacrylic acid esters and combinations thereof. Such free radically polymerizable compound include n-, sec-, or t-butyl methacrylate, hexyl methacrylate, 2-ethylhexyl methacrylate, octylmethacrylate, decyl methacrylate, lauryl methacrylate, cyclohexyl methacrylate, stearyl(meth)acrylate, allyl(meth)acrylate, glycerol tri(meth)acrylate, diethyleneglycol di(meth)acrylate, triethyleneglycol di(meth)acrylate, 1,3-propanediol di(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate tri(meth)acrylate; urethane (meth)acrylates; ((di)urethane dimethacrylate), the bis-(meth)acrylates of polyethylene glycols, and chlorine-, bromine-, fluorine-, and hydroxyl group containing monomers, for example, 3-chloro-2-hydroxylpropyl (meth)acrylate; reaction product of 2,2-Bis[4-(2-hydroxy-3-methacryloxypropoxy)phenyl] propane and a hexamethylene diisocyanate (HMDI)

Examples of carboxyl group-containing unsaturated monomers include, but are not limited to, such as acrylic acid, methacrylic acid, crotonic acid, itaconic acid, maleic acid, and fumaric acid.

Examples of $C_{2-8}$ hydroxyl alkyl esters of (meth)acrylic acid include, but are not limited to, 2-hydroxylethyl (meth)acrylate, 2-hydroxylpropyl (meth)acrylate, 3-hydroxypropyl (meth)acrylate, and hydroxybutyl (meth)acrylate.

Examples of $C_{2-18}$ alkoxyalkyl esters of (meth)acrylic acid include, but are not limited to, methoxybutyl methacrylate, methoxyethyl methacrylate, ethoxyethyl methacrylate, and ethoxybutyl methacrylate.

Olefins or diene compounds include, but are not limited, to ethylene, propylene, butylene, isobutene, isoprene, chloropropene, fluorine containing olefins and vinyl chloride.

Examples of monoesters may include monoesters between a polyether polyol (e.g., polyethylene glycol, polypropylene glycol or polybutylene glycol) and an unsaturated carboxylic acid (preferably methacrylic acid), monoesters or diesters between an acid anhydride group-containing unsaturated compounds (e.g., maleic anhydride or itaconic anhydride) and a glycol (e.g. ethylene glycol, 1,5-hexanediol or neopentyl glycol).

Examples of monoethers may include monoethers between a polyether polyol (e.g., polyethylene glycol, polypropylene glycol or polybutylene glycol) and a hydroxyl group-containing unsaturated monomer (e.g., 2-hydroxyl methacrylate).

Examples of adducts may include, but are not limited to, adducts between an unsaturated carboxylic acid and a monoepoxy compound; adducts between glycidyl (meth)acrylates (preferably methacrylate), a monobasic acid (e.g., acetic acid, propionic acid, p-t-butylbenzoic acid or a fatty acid).

Examples of vinyl monomers include, but are not limited to, aminopropyl vinyl ether, aminoethyl vinyl ether, N-vinyl formamide, vinylene carbonate, vinyl acetate, divinyl benzene, divinyl succinate, divinyl adipate, divinylphthalate, vinylpyridine, N-vinylpyrrolidone, vinyl carbazole, vinylidene halide, and vinyl (meth)acrylates.

Examples of styryl monomers include, but are not limited to, styrene and 2-methylstyrene.

(Meth)acrylamides may be selected from the following compounds: (meth)acrylamide, methylene bis-(meth)acrylamide, diacetone (meth)acrylamide,

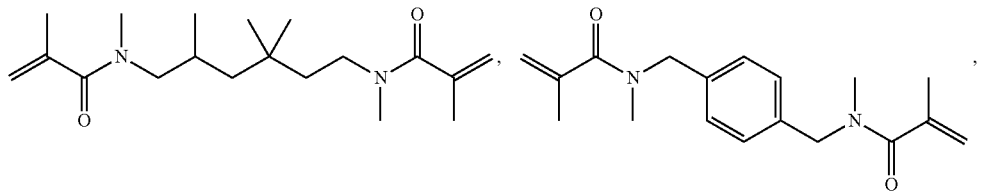

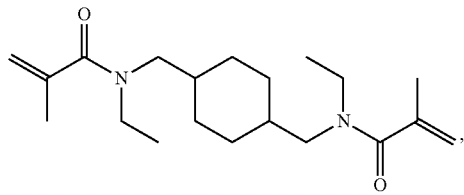

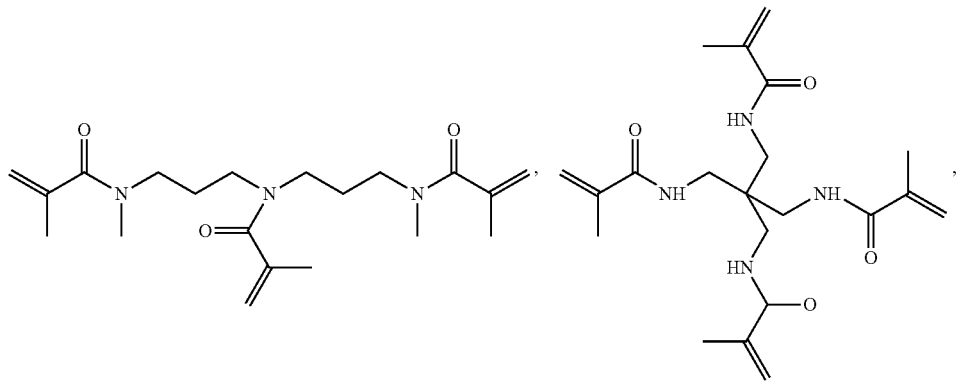

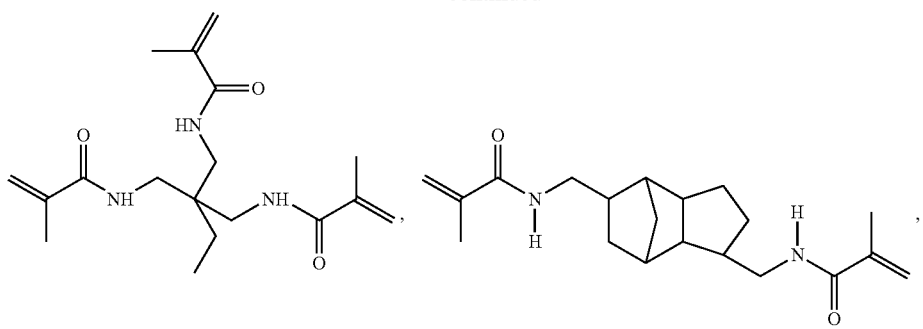
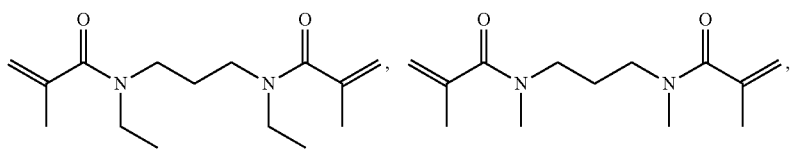
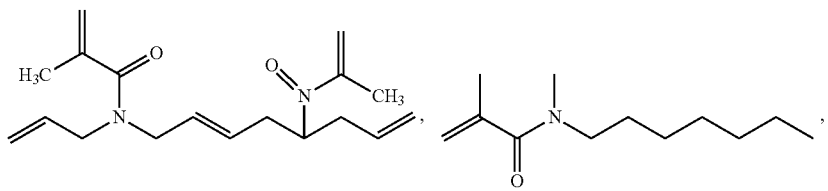
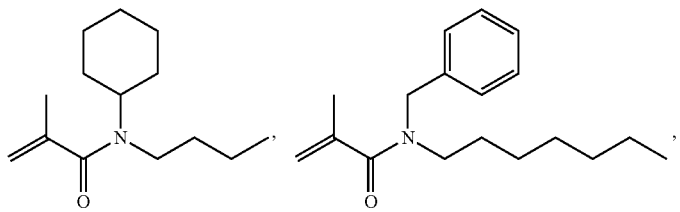
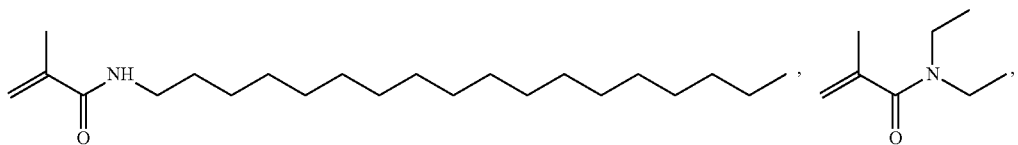
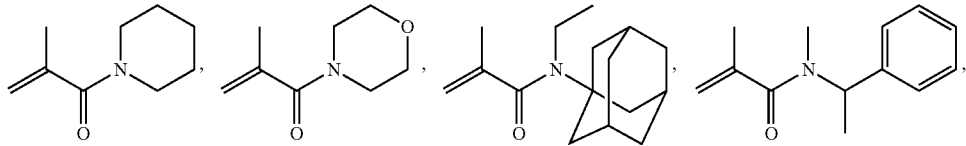
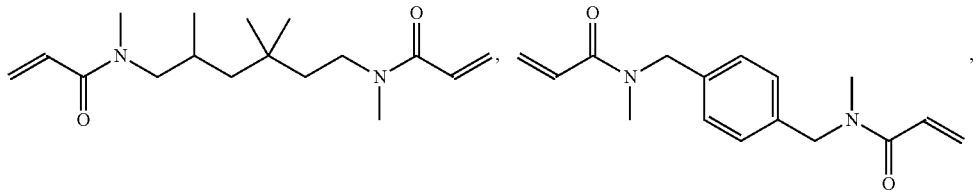
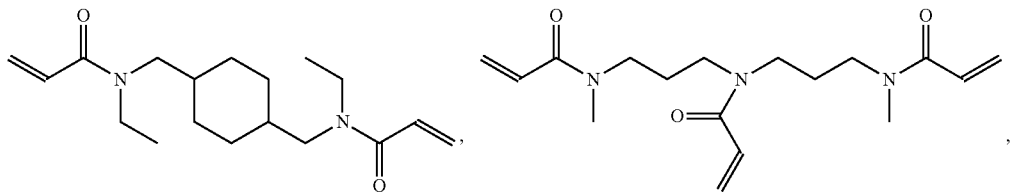

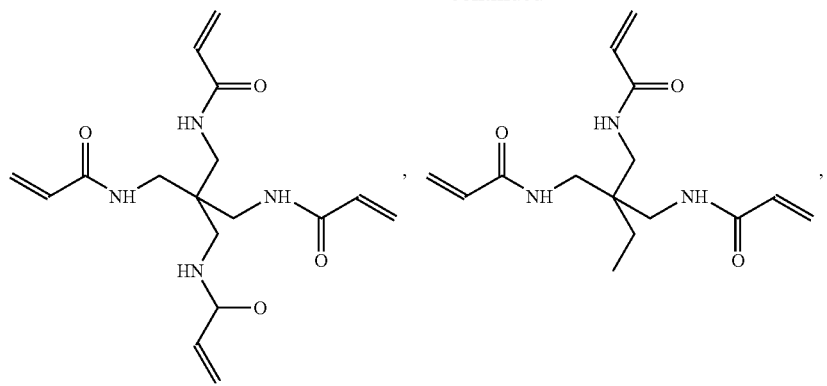
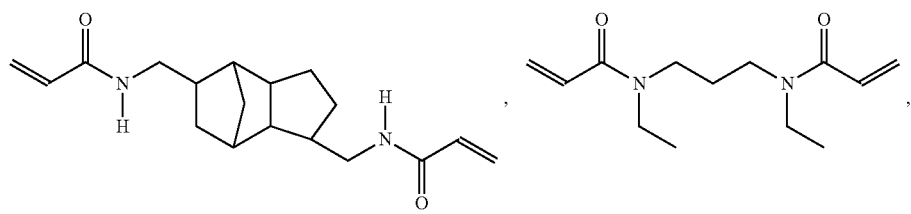
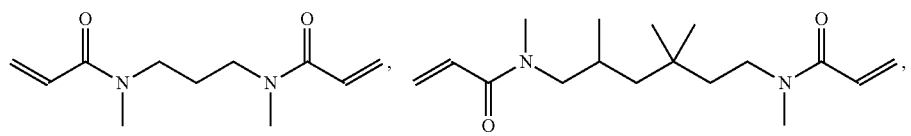
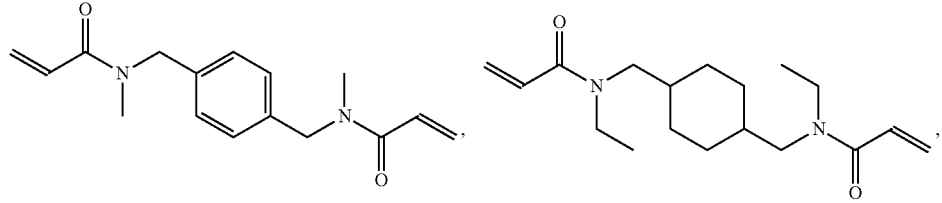
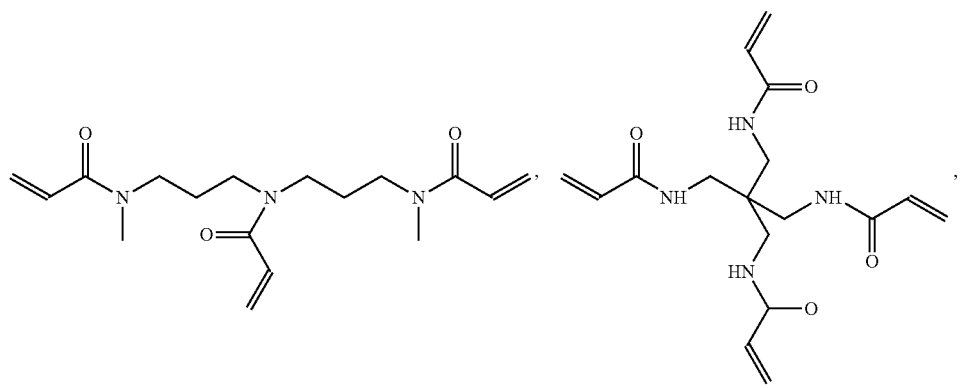
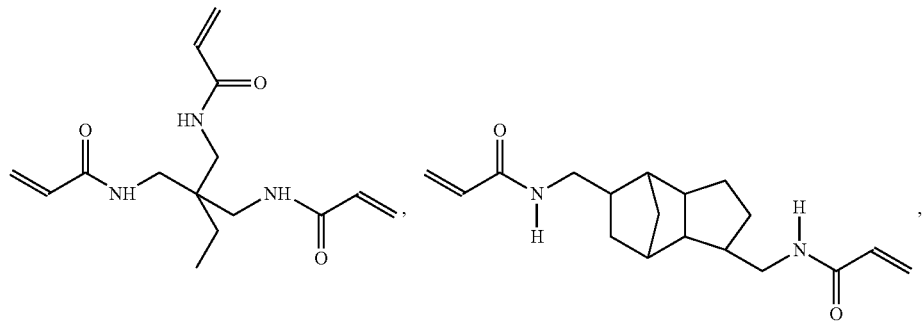

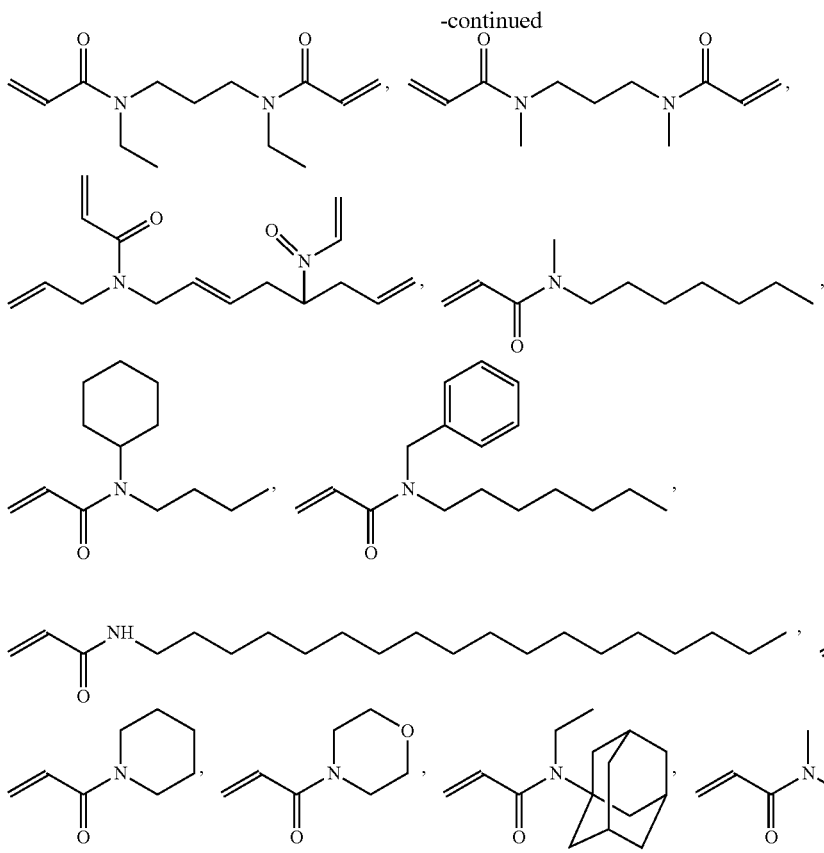

Further Components

The dental composition according to the present disclosure may comprise additional components, for example a ultra-violet stabilizer, one or more polymerization inhibitors, one or more solvents, colorants, fluorescent agents, opalescent agents, pigments, viscosity modifiers, fluoride-releasing agents, and combination thereof.

Examples of ultra violet stabilizers may include 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxy-benzophenone, 2-(2'-hydroxy-5'-methacryloxyethylphenyl)-2H-benzotriazole, phenothiazine, and HALS (hindered amine light stabilizers).

Typical polymerization inhibitors for a free radical system may include hydroquinone monomethyl ether (MEHQ), butylated hydroxytoluene (BHT), tert-butylhydroquinone (TBHQ), hydroquinone, phenol, 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, butyl hydroxyaniline, and the like. The inhibitors act as free radical scavengers to trap free radicals in the composition and to extend the shelf life stability of the dental material. The polymerization inhibitors, if present, may be present in amounts of from about 0.001 weight percent to about 1.5 weight percent of the dental material, such as from about 0.005 weight percent to about 1.1 weight percent or from about 0.01 weight percent to about 0.08 weight percent of dental material. The dental material may include one or more polymerization inhibitors.

The dental material of the present disclosure comprises a solvent mixture comprising water and an organic solvent. The solvent mixture may comprise one or more organic solvent(s).

The term "organic solvent" as used herein means any organic compound which is fluid or liquid at room temperature, and which is capable of dissolving or at least partly dissolving the components of the present dental composition. The organic solvent is suitably selected in view of its volatility and physiological harmlessness. Preferably, the organic solvent is more volatile than water, that is it has a vapour pressure higher than water at 20° C. Besides, it is preferred that the organic solvent is non-toxic for the patient to be treated, in particular for a human patient.

Preferably, the organic solvent of the solvent mixture is selected from the group consisting of n-propanol, iso-propanol, n-butanol, iso-butanol, sec-butanol, tert-butanol, acetone and methyl ethyl ketone. Preferably, the dental material comprises the solvent mixture in an amount of 25 to 50 percent by weight, more preferably 27 to 47 percent by weight, most preferably 29 to 44 percent by weight based on the total weight of the dental material.

It is preferred that the organic solvent comprised in the solvent mixture is n-propanol or iso-propanol, preferably iso-propanol.

Use of the Polymerizable Hydrolysis Stable Polycyclic Amide Monomer as Dental Materials A dental composition is prepared by mixing the components of the dental compositions of the present disclosure. The components of the dental composition can be combined (for example by mixing or blending) in a variety of manners and amounts in order to form the dental composition of the present disclosure.

Curable dental material compositions may contain
a) 1 to 99% w/w polymerizable hydrolysis stable polycyclic amide monomer;
b) 0.01 to 5% w/w of photoinitiator for radical polymerization; and
c) 1 to 99% polymerizable monomer.

The dental material of the present disclosure may be a composite, and may include a filler material in an amount from about 30 to about 90 percent by weight.

The dental material of the present disclosure may be an adhesive and may include a filler in an amount from about 50 to about 65 percent by weight, and solvent 0 to 70 percent by weight.

The dental material according to the disclosure may be a cement, and may include filler in an amount from about 50 to about 90 percent by weight The dental composite may be formulated by mixing the polymerizable hydrolysis stable polycyclic amide monomer matrix and a filler.

The disclosure will now be further illustrated by the following Examples.

EXAMPLES

Synthesis of a Hydrolysis Stable Bis (Norbornene Cyclopropane Amido) Compound 5.9 g (35 mmol) of Norbornene cyclopropane carbonyl chloride was dissolved in 75 mL dichloromethane and put in an ice bath. 2.7 g (17 mmol) of the diamine isomer mixture, TMHDA (CAS 25620-58-0) and 3.44 g (34 mmol) trimethylamine were dissolved in 20 mL dichloromethane and added dropwise to the reaction mixture. The reaction took place for 30 min at room temperature and was quenched by adding 150 mL water. The water layer was separated and washed 3 times with 50 mL dichloromethane. All organic layers were combined, dried and the solvent was removed under reduced pressure. Bis (Norbornene cyclopropane amido) compound (1) is a colorless solid. The product was characterized by $^1$H NMR spectrum, as depicted in FIG. 1

Application Example 1

Shrinkage Stress

Shrinkage stress was measured with a shrinkage stress measurement device, referred to as a tensometer, designed and fabricated at the Paffenbarger Research Center of the American Dental Association Foundation (ADAF). This device is based on the cantilever beam theory that bending force generated by a shrinking sample during polymerization causes the cantilever beam to deflect. Dental resin or composite are injected into a cell between two glass rods with 6.0 mm in diameter and 2.25 mm in thickness. The material is cured with a QHL-75 halogen lamp at a light intensity of 400 mW/cm$^2$ for 60 seconds. A more detailed description, experimental procedure, and characterization of the tensometer are discussed in (H. Lu et al., Journal of Materials Science, Materials in Medicine, 2004, Vol. 15, 1097-1103), which is hereby incorporated by reference in its entirety.

Copolymerization of Bis(Norbornene Cyclopropane Amido) Compound (1) with Triethylene Glycol Dimethacrylate (TEGDMA)

In order to determine the polymerization shrinkage, stress a mixture of ingredients as shown in Table 1, were mixed and then irradiated with a visible light source.

| Ingredients of HLU18-150-N5T5 | % by wt | M[g/mol] | % by mol | mass[g] | Lot# | C=C amount [g/mol] |
|---|---|---|---|---|---|---|
| Bis(Norbornene cyclopropane amido)compound (1) | 49.45 | 422.60 | 0.395 | 1.2363 | 13681 | 2.34 |
| TEGDMA | 49.45 | 286 | 0.584 | 1.2363 | 161103 | 3.46 |
| CQ | 0.50 | 166.22 | 0.01 | 0.0125 | 140618 | |
| EDAB | 0.60 | 193.24 | 0.01 | 0.0149 | 140914 | |
| Total | 100 | | | | | 5.80 |

Figure 2:
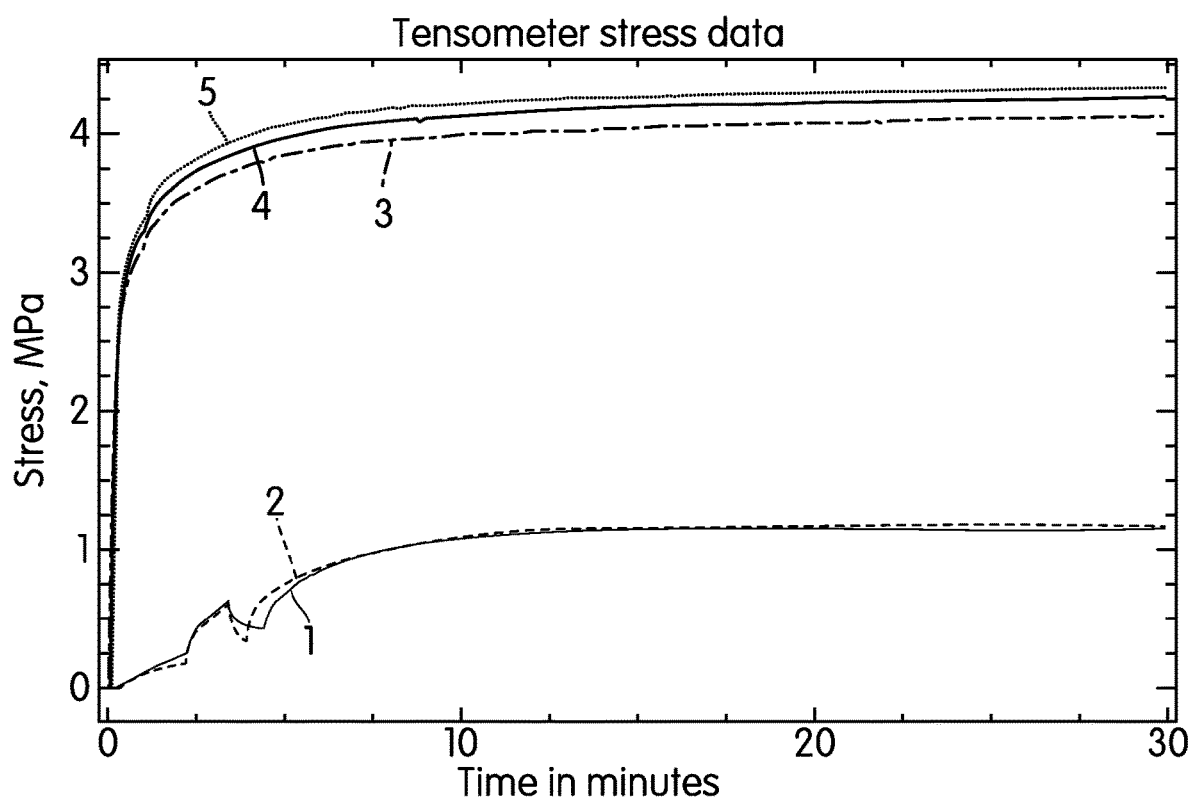
FIG. 2 depicts polymerization shrinkage stress data comparison of bis(Norbornene cyclopropane amido) compound 1 (HLU18-150-N5T5) w.r.t CMX-Resin.

The maximum shrinkage stress for ingredients of HLU18-150-N5T5 was 1.5 MPa (as shown in FIG. 2).

Comparision Example

CMX-Resin was evaluated for shrinkage stress, the maximum shrinkage stress was observed to be 4.5 MPa (shown in FIG. 2); CMX-Resin also displayed much higher shrinkage stress development rate.

While the present disclosure has been described with reference to one or more embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims. In addition, all numerical values identified in the detailed description shall be interpreted as though the precise and approximate values are both expressly identified.

The invention claimed is:
1. A dental material comprising:
(i) a polymerizable hydrolysis stable polycyclic amide monomer comprising a compound of Formula (I)

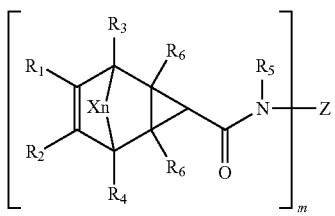

Formula (I)

wherein
$R_1$, $R_2$, $R_3$ and $R_4$ are independent from each other, and represent a hydrogen, a $C_{1-4}$ alkyl group or a $C_5$-$C_{18}$ aryl group;
$R_5$ is a hydrogen atom, a $C_{1-6}$ alkyl group, a $C_{3-10}$ cycloalkyl group, a $C_7$-$C_{12}$ aralkyl group;
wherein each group of $R_5$ is optionally substituted by one or more of a $C_{1-4}$ alkyl group, a $C_{1-4}$ alkoxy group, or a hydroxyl group;
$R_6$ is a hydrogen atom, a $C_{1-6}$ alkyl group, a $C_{3-10}$ cycloalkyl group, a $C_1$-$C_{12}$ aralkyl group, a $C_6$-$C_{10}$ aryl group, an ester or an amide group,
X is an alkylene group, O, S, or CO;
n is an integer of from 0 to 1;
m is an integer of from 1 to 6; and
Z is an m valent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or an unsubstituted or substituted $C_3$-$C_{18}$ heteroarylene group; wherein each unsubstituted or substituted group of Z optionally includes at least one of 1-6 oxygen, silicon, sulfur atoms, or $NR_9$, wherein $R_9$ represents a hydrogen atom, straight or branched or cyclic $C_{1-6}$ alkyl groups;
(ii) at least one polymerizable resin monomer having at least one (meth) acrylate group, (meth) acrylamide group, allyl group or vinyl group;
(iii) optionally a particulate filler; and
(iv) at least one of a photoinitiator and a redox initiator.

2. The dental material according to claim 1, wherein $R_1$, $R_2$, $R_3$, $R_4$ and $R_6$ is a hydrogen; X is alkylene and n is 1.

3. The dental material according to claim 1, wherein $R_1$, $R_2$, $R_3$, $R_4$, $R_5$ and $R_6$ is a hydrogen; X is alkylene, m is 1 and n is 1.

4. The dental material according to claim 1, wherein Z represent a group of Formula IV, V, or VI

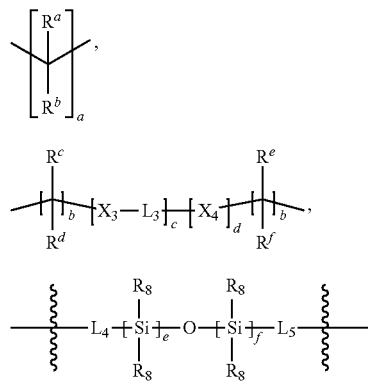

Formula IV

Formula V

Formula VI wherein
$R^a$, $R^b$, $R^c$, $R^d$, $R^e$ and $R^f$ are independently a same or different hydrogen atom, a $C_{1-6}$ linear or branched alkyl group, or a $C_{4-10}$ aryl group;
$R_8$ represent a straight chain, branched or cyclic alkyl group;
$X_3$ and $X_4$ are independently a same or different oxygen atom, a sulfur atom or a group $NR_9$, wherein $R_9$ is a hydrogen atom or a $C_{1-4}$ alkyl group;
$L_3$ is a divalent hydrocarbon radical selected from linear or branched $C_{2-3}$ alkylene group or $C_5$-$C_{18}$ arylene group;
$L_4$ and $L_5$ are independently a same or different $C_{2-20}$ alkylene group;
a is an integer of from 1 to 18;
b is an integer of from 1 to 10;
c is an integer of from 1 to 10;
d is an integer of from 0 to 1,
e is an integer of from 1 to 10; and
f is an integer of from 0 to 1.

5. The dental material according to claim 1, wherein the compound of formula (I) is obtained by reacting a mixture comprising:
(i) x equivalent of at least one component A having compound of Formula (II)

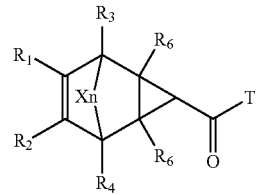

Formula II wherein
$R_1$, $R_2$, $R_3$ and $R_4$ are independent from each other, and represent a hydrogen, a $C_{1-4}$ alkyl group or a $C_5$-$C_{18}$ aryl group;
$R_6$ is a hydrogen atom, a $C_{1-6}$ alkyl group, a $C_{3-10}$ cycloalkyl group, a $C_7$-$C_{12}$ aralkyl group, a $C_6$-$C_{10}$ aryl group, an ester or an amide group,
X is an alkylene group, O, S, or CO;
n is an integer of from 0 to 1; and
T is a hydroxyl group or a halogen atom,
(ii) y equivalent of a component B having at least one of primary amine functional group and secondary amine functional group of compounds of Formula III:

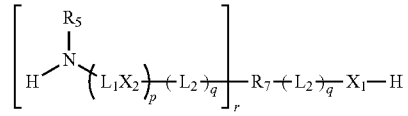

Formula III wherein
$R_7$ is a (r+1)-valent aliphatic $C_{2-10}$ group, cycloaliphatic $C_3$-$C_6$ group or an aralkylene group having 7 to 24 carbon atoms, wherein each group of Ry optionally contains oxygen or sulfur atoms and each group of $R_7$ is optionally substituted by $C_{1-4}$ alkyl groups;
$R_5$ is a hydrogen atom, a $C_{1-6}$ alkyl group, a $C_{3-10}$ cycloalkyl group, a $C_7$-$C_{12}$ aralkyl group, or an (meth) acryl group; wherein each group of $R_5$ is optionally substituted by one or more of a $C_{1-4}$ alkyl group, a $C_{1-4}$ alkoxy group, or a hydroxyl group;

$L_1$ and $L_2$ are independently a same or different straight or branched chain alkylene having from 1 to 4 carbons;

$X_1$ is a direct bond, or a nitrogen atom substituted by $R_5$;

$X_2$ is an oxygen atom;

p and q are an integer of from 0 to 4; and r is an integer of from 1 to 6, wherein x and y are molar equivalents of a component (i) and (ii).

6. The dental material according to claim 1, wherein the at least one polymerizable resin monomer is selected from the group consisting of 2,2'-bis [4-(3-methacryloxy-2-hydroxypropoxy)-phenyl] propane (bis-GMA), tetraethyleneglycoldi (meth) acrylate (TEGDMA), urethane dimethacrylate (UDMA), trimethylolpropane trimethacrylate, $C_1$-$C_{20}$alkyl (meth) acrylates, an aromatic methacrylate, and a hydroxy alkyl (meth)acrylate.

7. The dental material according to claim 1, wherein the polymerizable hydrolysis stable polycyclic amide monomer is present in an amount of from 1 to 99% w/w based on total weight of the dental material.

8. The dental material according to claim 1, wherein the at least one of photoinitiator and redox initiator is present in an amount of from 0.01 to 5% w/w based on total weight of the dental material.

9. The dental material according to claim 1, wherein the at least one polymerizable resin monomer is present in an amount of from 1 to 99% w/w based on total weight of the dental material.

10. The dental material according to claim 1, wherein the dental material is a dental composite or a dental cement and includes a particulate filler.

11. The dental material according to claim 10, wherein the particulate filler is present in an amount of from 10 to 90% w/w based on total weight the dental composite material.

12. The dental material according to claim 1, further comprising a stabilizer, one or more polymerization inhibitor(s), one or more solvents, and combinations thereof.

13. A cured dental material obtained by polymerizing a mixture comprising:

(i) a polymerizable hydrolysis stable polycyclic amide monomer comprising compound of Formula (I)

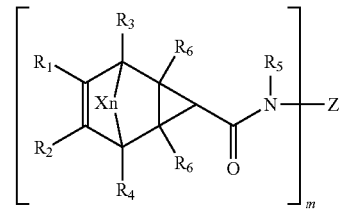

Formula (I)

wherein $R_1$, $R_2$, $R_3$ and $R_4$ are independent from each other, and represent a hydrogen, a $C_{1-4}$ alkyl group or a $C_5$-$C_{18}$ aryl group;

$R_5$ is a hydrogen atom, a $C_{1-6}$ alkyl group, a $C_{3-10}$ cycloalkyl group, a $C_7$-$C_{12}$ aralkyl group;

wherein each group of $R_5$ is optionally substituted by one or more of a $C_{1-4}$ alkyl group, a $C_{1-4}$ alkoxy group, or a hydroxyl group;

$R_6$ is a hydrogen atom, a $C_{1-6}$ alkyl group, a $C_{3-10}$ cycloalkyl group, a $C_7$-$C_{12}$ aralkyl group, a $C_6$-$C_{10}$ aryl group, an ester or an amide group, X is an alkylene group, O, S, or CO;

n is an integer of from 0 to 1;

m is an integer of from 1 to 5; and

Z is an m valent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or an unsubstituted or substituted $C_3$-$C_{18}$ heteroarylene group; wherein each unsubstituted or substituted group of Z optionally includes at least one of 1-6 oxygen silicon, sulfur atoms, or $NR_9$, wherein $R_9$ represents a hydrogen atom, straight or branched or cyclic $C_{1-6}$ alkyl groups;

(ii) at least one polymerizable resin monomer having at least one (meth) acrylate group, (meth) acrylamide group, allyl group or vinyl group;

(iii) optionally a particulate filler; and (iv) at least one of a photoinitiator and a redox initiator.

* * * * *

UNITED STATES PATENT AND TRADEMARK OFFICE
CERTIFICATE OF CORRECTION

PATENT NO. : 12,396,929 B2
APPLICATION NO. : 17/601786
DATED : August 26, 2025
INVENTOR(S) : Ritter et al.

Page 1 of 1

It is certified that error appears in the above-identified patent and that said Letters Patent is hereby corrected as shown below:

In the Claims

In Column 31, Line 38, in Claim 1, delete "(meth) acrylate" and insert --(meth)acrylate-- therefor In Column 31, Line 38, in Claim 1, delete "(meth) acrylamide" and insert --(meth)acrylamide-- therefor In Column 32, Line 62, in Claim 5, delete "Ry" and insert --$R_7$-- therefor In Column 33, Lines 14-15, in Claim 6, delete "tetraethyleneglycoldi (meth) acrylate" and insert --tetraethyleneglycoldi(meth)acrylate-- therefor In Column 33, Line 17, in Claim 6, delete "$C_1$-$C_{20}$alkyl (meth) acrylates," and insert --$C_1$-$C_{20}$alkyl(meth)acrylates,-- therefor In Column 34, Line 39, in Claim 13, delete "(meth) acrylate" and insert --(meth)acrylate-- therefor In Column 34, Line 39, in Claim 13, delete "(meth) acrylamide" and insert --(meth)acrylamide-- therefor Signed and Sealed this
Second Day of December, 2025

John A. Squires
*Director of the United States Patent and Trademark Office*